United States Patent
Gau et al.

[11] Patent Number: 5,084,061
[45] Date of Patent: Jan. 28, 1992

[54] INTRAGASTRIC BALLOON WITH IMPROVED VALVE LOCATING MEANS

[76] Inventors: Fred C. Gau, 14812 Imperial Dr., Libertyville, Ill. 60048; John C. Hancock, 449 Paseo del Descanso, Santa Barbara, Calif. 93105

[21] Appl. No.: 394,545

[22] Filed: Aug. 16, 1989

Related U.S. Application Data

[63] Continuation of Ser. No. 100,917, Sep. 25, 1987, abandoned.

[51] Int. Cl.⁵ ............................................. A61M 29/00
[52] U.S. Cl. .................................... 606/195; 606/192; 604/96; 604/103
[58] Field of Search ................... 128/344, 303 R; 604/96–103

[56] References Cited

U.S. PATENT DOCUMENTS

| | | | |
|---|---|---|---|
| 1,008,641 | 11/1911 | Coregory | 137/223 |
| 1,702,974 | 2/1929 | MacDonald | 137/223 |
| 2,073,766 | 3/1937 | Suzuki | 137/223 |
| 2,700,980 | 2/1955 | Andrews | 137/223 |
| 4,416,267 | 11/1983 | Garren et al. | 128/344 X |
| 4,462,449 | 7/1984 | Zabel | 137/223 X |
| 4,485,805 | 12/1984 | Foster | 128/344 X |
| 4,648,383 | 3/1987 | Angelchik | 128/303 R X |
| 4,694,827 | 9/1987 | Weiner et al. | 128/344 X |
| 4,723,547 | 2/1988 | Kullas et al. | 128/344 X |

Primary Examiner—John D. Yasko
Assistant Examiner—Corrine Maglione
Attorney, Agent, or Firm—Michael G. Petit

[57] ABSTRACT

An intragastric balloon has an ellipsoid or like configuration so that the balloon implanted in the stomach tends to rotate or rock only about one axis when a surgeon attempts to manipulate the balloon, for example, for the purpose of finding a filler valve and inserting a filler tube into it. For easy location, the filler valve is disposed on the equator. A retrieval tab is mounted to the exterior of the balloon, to permit capturing of the balloon and retrieval from the stomach, after the balloon has been deflated and is no longer desired for weight control purposes. Visual and X-ray opaque markers are located in the proximity of the valve and of the retrieval tab to facilitate their visualization with an endoscopic light when the balloon is in the stomach.

41 Claims, 1 Drawing Sheet

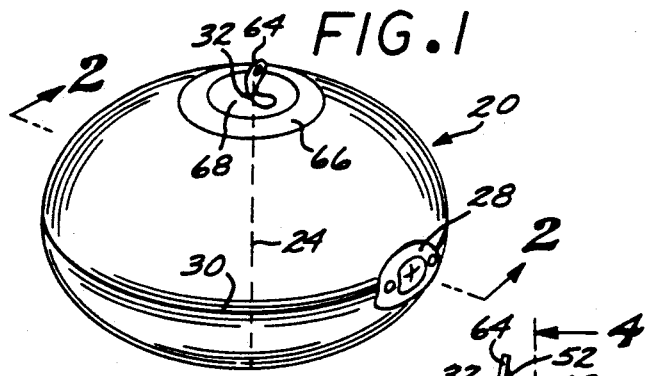
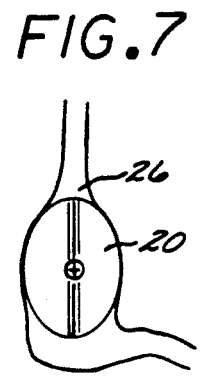
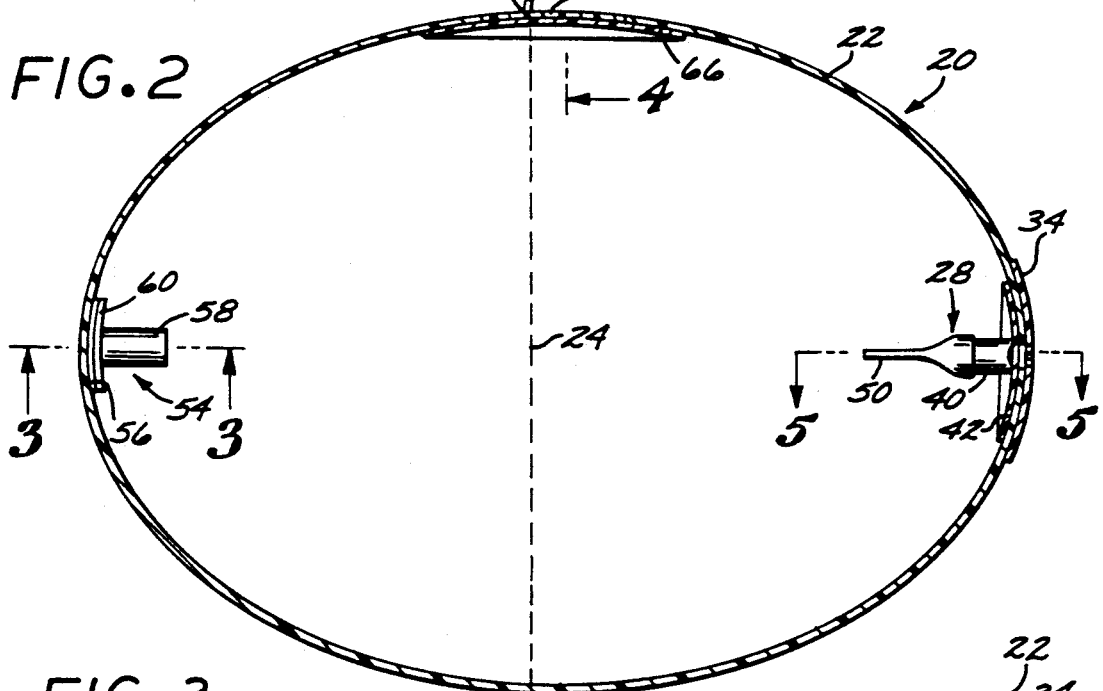
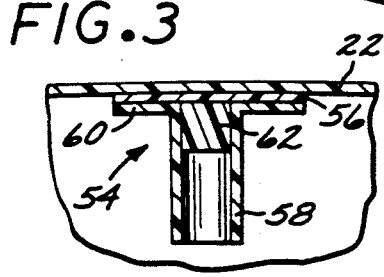
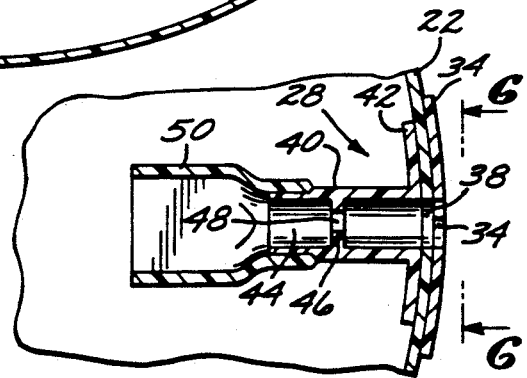
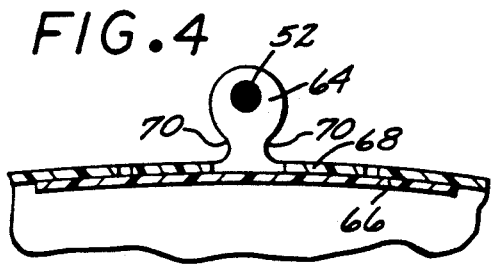
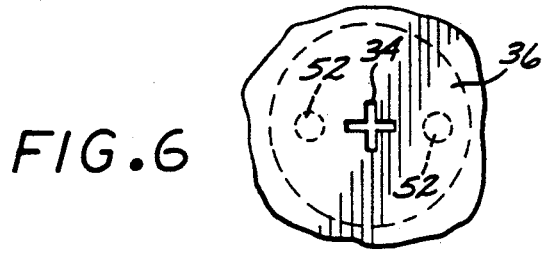

INTRAGASTRIC BALLOON WITH IMPROVED VALVE LOCATING MEANS

CROSS-REFERENCE TO RELATED APPLICATION

The present application is a continuation of application Ser. No. 07/100,917, filed Sept. 25, 1987, now abandoned.

BACKGROUND OF THE INVENTION

1. Field of the Invention

The present invention is in the field of implantable weight control devices. More particularly, the present invention is directed to a gastric balloon which has certain improved features enabling a surgeon to locate a filler valve and retrieval tabs on the exterior of the balloon with substantial ease while the balloon is in the stomach.

2. Brief Description of the Prior Art

Gastric balloons used for achieving loss of weight in extremely obese persons have been known in the prior art. All gastric balloons utilized for this purpose function on the principle that an empty bag or balloon is placed into the stomach through the esophagus. Thereafter, the bag or balloon is filled (fully or partially) with a suitable fluid, such as saline solution, through a filler tube which is inserted into the stomach through the mouth or the nose. The balloon occupies space in the stomach thereby leaving less room available for food and creating a feeling of satiety for the obese person. Clinical experience of the prior art has shown that for many obese patients the intragastric balloons significantly help to control appetite and accomplish weight loss.

Among the intragastric bags or balloons described in the prior art, one type remains connected to a filler tube during the entire time period while the balloon is in the stomach. The tube is introduced into the patient's stomach through the nostrils. Such an intragastric balloon is described, for example, in U.S. Pat. No. 4,133,315.

A second type of intragastric balloon of the prior art is placed into the stomach with the assistance of an appropriate plastic tube and usually a stylette. The balloon is filled with saline, whereafter the tube and stylette are withdrawn from the stomach. An intragastric balloon of the second type is described, for example, in UK Patent Application GB 2 090 747. The balloon of this UK patent reference, like many intragastric balloons of the prior art, is substantially spherical in configuration.

Even for the balloons of the second type, it may become desirable, from time-to-time, to add more saline in order to further expand the balloon to optimize weight control. Even more importantly, it is desirable for such balloons to become deflated through a tube before the empty balloon is removed from the stomach through the esophagus, or is allowed to pass "normally" through the digestive system.

To accomplish the foregoing, intragastric balloons of the second type are normally equipped with a self-sealing valve into which the filler tube can be inserted. One difficulty frequently encountered in the prior art is related to finding the valve when the balloon is already in the stomach and the surgeon is attempting to reinsert the filler tube for the purpose of adding or removing fluid from the balloon. Those experienced in the art will readily appreciate that a small endoscopic light which can be lowered into the stomach for the procedure causes the surface of the balloon to shine in such a manner that visually locating the valve is rather difficult and the process of searching for the valve undesirably prolongs the surgical procedure. Moreover, even after the filler valve has been visually located, it is often still difficult or awkward for the surgeon to reinsert the tube into the filler valve. This is because the balloon is slippery and positionally unstable. In other words, the usually spherical (or substantially spherical) intragastric balloons readily rotate in the stomach, so that even a slight disturbance of the balloon may place the filler valve into virtually any possible position relative to the filler tube poised to engage it.

For further and detailed information regarding intragastric balloons and related inflatable bags or the like designed for implantation into the human body, reference is made to the following patents and/or patent applications: U.S. Pat. Nos. 4,416,267; 4,485,805; 4,311,146; 4,236,521; 2,470,665; 3,046,988; 157,343; Published PCT Application No. PCT/US79/00354, and UK Patent Specification No. 1333096. The following articles or publications are also of interest: "Intragastral applizierter Ballon zur Behandlung der Adipositas", Deutsche Medizinische Wochenschrift (DMW), 1983, No. 8, page 315; "Intragastraler Appetit-depressor", Balloon Munch. Med. Wochenschrift 124 (1982), No. 2, page 39; "Der Magenballon in der behandlung der Adipositas permagna", Deutsche Medizinische Wochenschrift, 1984 No. 31/32, page 1200; "Intragastrick ballon som adipositasbehandling", UGESKY. LEGER 144/6, February, 1982, page 394; and the article by Joanne Richard titled "Gastric bubble battles bulge".

In light of the above-noted and other shortcomings of the prior art, there is a need in the art for an intragastric balloon which has a readily locatable filler valve and other improved properties. The present invention provides such an intragastric balloon.

SUMMARY OF THE INVENTION

It is an object of the present invention to provide an intragastric balloon having a self-sealing valve which is accessible to a filler tube to affect further inflation or deflation even while the balloon is in the stomach.

It is another object of the present invention to provide an intragastric balloon having a self-sealing valve which can be readily located visually prior to insertion of a filler tube, even while the balloon is in the stomach.

It is still another object of the present invention to provide an intragastric balloon, the position of which in the stomach is relatively stable and non-traumatic to the patient due to the configuration of the balloon itself.

It is yet another object of the present invention to provide an intragastric balloon which, when no longer desired can be readily deflated and removed from the stomach.

It is a further object of the present invention to provide an intragastric balloon having an efficient self-sealing filler valve, which substantially prevents entry of foreign matter into the interior of the balloon.

The foregoing and other objects and advantages are attained by an inflatable intragastric balloon which has an inflatable shell of such configuration that after inflation the shell has a unique axis of greatest symmetry, whereby when the inflated balloon is placed into the interior of the stomach, disturbance of the balloon is likely to cause spinning or rocking of the balloon only about its unique axis of greatest symmetry, because such motion involves a minimum displacement of the walls of the stomach and therefore presents the path of least resistance. Preferably, the inflated balloon has the shape of an ellipsoid which satisfies the foregoing requirement.

The balloon has a self-sealing valve into which a filler tube can be inserted either for inflation or deflation. The filler valve is located on the shell substantially on the equator of the ellipsoid. Visual and X-ray opaque markers are located adjacent to the filler valve to facilitate location of the filler valve in the stomach.

A tab, having visual and X-ray opaque markers, is located on the exterior of the shell of the balloon to facilitate capturing the balloon with a loop or the like for removal from the stomach.

The features of the present invention, together with further objects and advantages, can be best understood from the following description taken together with the accompanying drawings.

BRIEF DESCRIPTION OF THE DRAWINGS

FIG. 1 is a perspective view of the preferred embodiment of the intragastric balloon of the present invention;

FIG. 2 is a cross-sectional view of the preferred embodiment, the cross-section being taken on line 2,2 of FIG. 1;

FIG. 3 is a partial cross-sectional view taken on lines 3,3 of FIG. 2, the view showing a filler tube guide assembly adapted to receive a stylette used during insertion of the balloon into the stomach;

FIG. 4 is a partial cross-sectional view taken on lines 4,4 of FIG. 2, the view showing a retrieval tab assembly affixed on the exterior of the preferred embodiment;

FIG. 5 is a partial cross-sectional view taken on lines 5,5 of FIG. 2, the view showing a self-sealing valve assembly of the preferred embodiment;

FIG. 6 is a partial view of the exterior of the valve assembly of the preferred embodiment, and FIG. 7 is a schematic view showing the balloon of the present invention disposed in the stomach.

DESCRIPTION OF THE PREFERRED EMBODIMENT

The following specification, taken in conjunction with the drawings, sets forth the preferred embodiment of the present invention. The embodiments of the invention disclosed herein are the best modes contemplated by the inventors for carrying out their invention in a commercial environment, although it should be understood that various modifications can be accomplished within the parameters of the present invention.

Referring now to the drawing Figures and particularly to the perspective view of FIG. 1, a preferred embodiment of the intragastric balloon 20 of the present invention is disclosed. As it was noted in the introductory section of the present application for United States patent, intragastric balloons are inserted into the stomach of chronically or extraordinarily obese persons for the purpose of facilitating weight reduction by such persons. The intragastric balloon 20 of the invention, as well as the balloons of the prior art, is placed into the stomach in a non-inflated form, and is filled after insertion with a suitable fluid, such as saline solution. Whereas the mere concept of using intragastric balloons for weight reduction is not new, the herein-described intragastric balloon has several novel features which facilitate the insertion, inflation, deflation, and retrieval of the balloon. These features are described here in detail. On the other hand, standard features of the balloon are described here only to the extent considered necessary to explain and emphasize the novel features.

The intragastric balloon 20 comprises an inflatable elastomeric shell 22, which is preferably made from silicone rubber cast on a mandrel (not shown) to have a final thickness of approximately 0.006 to 0.025 inches. Still more preferably, the shell 22 comprises silicone rubber material containing a high percentage of phenyl groups.

The configuration of the balloon 20, or stated in other words, the configuration of the inflated shell 22, is an important novel feature of the present invention. Generally speaking, the intragastric balloons of the prior art are spheres. In contrast to the prior art, the intragastric balloon 20 of the present invention has such a configuration that when the balloon 20 is submerged in a liquid, or floats on the surface of a liquid, or is pressed on by the walls of a stomach, a disturbance causes the balloon to spin or rock primarily only about one unique axis. Preferably, among the several geometric configurations which may meet this requirement, the balloon has the ellipsoid configuration shown on FIG. 1.

The ellipsoid configuration of the preferred embodiment of the balloon 20 has a shorter axis 24 which is shown with dotted lines on FIGS. 1 and 2. The shorter axis 24 is the single unique axis of greatest symmetry. It should be readily apparent from the foregoing, and from a consideration of FIGS. 1 and 7, that when the ellipsoid balloon 20 of the herein-described preferred embodiment is disposed within the walls of a stomach and disturbed, for example, touched by a filler tube (not shown) in an effort to spin or rotate the device to find a self-sealing valve, then the balloon 20 is likely to principally spin or rock only about the shorter axis 24. This feature greatly facilitates a surgeon's work when the balloon 20 is in the stomach 26 and when the surgeon (not shown) must rely on a small endoscopic light (not shown), surgical optics (not shown), and tools (not shown) to see, locate, and manipulate the hereinafter-described components of the balloon 20. Thus, in accordance with the present invention the surgeon only needs to rotate the balloon 20 about its shorter axis to locate the valve 28.

In contrast with the above-described configuration of the balloon 20 of the present invention, the spherical intragastric balloons of the prior art are likely to spin or rock about a limitless multitude of possible axes. Therefore, the location and manipulation of valves and other components of these prior art balloons is quite difficult when the balloon is in the stomach.

Referring now primarily to FIGS. 1 and 2 of the drawings, a self-sealing valve 28 of the balloon 20 of the present invention is shown. The purpose of the valve 28 is to permit inflation of the balloon 20 after it has been inserted into the stomach 26, and also its deflation before it is desired to remove the balloon 20 from the stomach 26. Sometimes, it is also necessary or desirable to add or withdraw liquid from the balloon 20 while the balloon 20 remains in the stomach 26. Adding or withdrawing liquid to the balloon 20 occurs, for example, when the treatment with the intragastric balloon 20 involves inflation or deflation in increments whereby a gradually changing space is occupied by the balloon 20 in the bearer's stomach 26. This is done to optimize treatment for an individual patient.

It is an important feature of the present invention that the self-sealing valve 28 is placed into a definite, predetermined position relative to the axis of greatest symmetry of the balloon 20. Preferably, the self-sealing valve 28 is placed on, or in the close vicinity of the equator 30 of the ellipsoid ballon 20, as is shown on the appended drawing Figures. For the several geometric configurations possible for the balloons 20 of the present invention, the position of the equator 30 can be described in more general terms as the line where a plane perpendicular to the axis of greatest symmetry intersects the surface of the inflated shell 22, provided such plane halves the axis of greatest symmetry.

The combined effects of the above-described unique configuration of the balloon 20 and of the unique valve 28 location substantially on the equator 30, render it relatively easy for a surgeon (not shown) to find the valve 28 even when the balloon is in the stomach 26. Likewise, it is relatively easy for the surgeon (not shown) to manipulate the balloon 20 and to insert a filler tube (not shown) into the valve 28 for the purpose of inflating or deflating the balloon 20.

Several kinds of self-sealing filler valves known in the art may be used in the intragastric balloon 20 of the present invention. However, the preferred embodiment of the present invention employs a self-sealing valve 28 which provides excellent results in terms of reliability of operation and ability to keep contaminations, such as food particles and stomach contents, out of the interior of the balloon 20. The self-sealing valve 28 of the preferred embodiment is believed to be novel and unique on its own right, and is described below in detail as follows.

The valve 28 includes a valve cover patch 34 which is affixed to the exterior of shell 22 by using a suitable adhesive, or by vulcanization, or both. The valve cover patch 34, like substantially all components of the intragastric balloon 20, is made from silicone rubber, and in the herein-described preferred embodiment comprises a patch of approximately 12 mm in diameter. In the assembled balloon 20 the valve cover patch 34 has a substantially X-shaped slot 36. The center of the slot 36 is aligned with a round opening or hole 38 in the shell 22 itself. The hole 38 in the shell 22 of the preferred embodiment is approximately 2.5 mm in diameter, which is larger than the central opening in the valve cover patch 34 created by the presence of the X-shaped slot 36. The diameter of the hole 38 is larger than the external diameter of a filler tube (not shown) which is to be inserted through the hole 38. Consequently, the filler tube (not shown) moves through the hole 38 without friction. This facilitates inserting the filler tube (not shown) into the valve 28 when the device is in the stomach.

A valve stem assembly comprising a tubular valve stem 40, and a flange 42, is affixed by a suitable adhesive (RTV 3140 of Dow Corning Corp.) to the interior of the shell 22. An internal duct 44 of the tubular valve stem 40 is also approximately 2.5 mm in diameter and is in axial alignment with the hole 38 of the shell 22. The valve stem 40 is approximately 12 mm long, and a membrane 46 is disposed in approximately the middle of its interior. Save for a relatively small hole, or preferably an X-shaped slot 48, the membrane 46 interferes with passage of solid objects through the duct 44 of the tubular valve stem 40. A leaf valve (also known as a duck bill valve) comprising a relatively flat piece of silicone elastomer 50 is affixed by adhesive to the end of the valve stem 40. The silicone elastomer 50 which comprises the leaf valve of the preferred embodiment is approximately 1.00 inch long, 0.4 inch (10.2 mm) wide, and 0.040 inch high at its end remote from the valve stem 40.

Operation of the entire self-sealing valve assembly 28 should be readily apparent to those skilled in the art in light of the foregoing description. The filler tube (not shown), which is usually a plastic tube containing a stainless steel or like rigid stiffening rod stylette (not shown) in its center, is inserted through the X-shaped slot 36, through the hole 38, through the tubular valve stem 40, through the second X-shaped slot 48 in the membrane 46, and through the leaf valve 50 until the filler tube is in the interior of the shell 22. In such a position, both addition and withdrawal of liquid can be accomplished. For addition of liquid only, the filler tube does not need to penetrate through the leaf valve 50. The structure of the valve permits addition of liquid and also withdrawal of liquid with the filler tube (not shown) without leakage and without significant danger that foreign materials can penetrate through the valve 28 into the interior of the balloon 20. The fact that the internal lumen of the valve stem is larger than the diameter of the fill tube (not shown) aids in thrusting the filler tube into the valve 28.

As an additional novel feature, a visual and X-ray opaque marker is placed in the vicinity of the self-sealing valve 28 to render it relatively easy for a surgeon (not shown) to locate the valve 28 when the balloon 20 is in the stomach 26. As is known, while attempting to manipulate the balloon 20 in the stomach 26, the surgeon (not shown) uses a small endoscopic light (not shown) and an optical system, commonly known as an illuminated flexible gastroscope (not shown), which permits him to see within the interior of the stomach 26.

In the herein-described preferred embodiment, the marker comprises two black tantalum metal-containing dots 52 affixed on the flange of the 42 valve stem 40, and disposed within the interior of the shell 22. The tantalum containing dots 52 comprise, in the preferred embodiment, a mixture of silicone rubber adhesive and tantalum metal powder, for example in ratios of 4 to 1. This mixture readily adheres to the silicone rubber. By virtue of its tantalum content the marker is black and highly visible, and is also X-ray opaque. The shell 20 can also include a visible, preferably radio-opaque line or mark around the equator 30.

Referring now primarily to FIGS. 2 and 3 of the appended drawings, a fill tube guide 54 is shown mounted in the interior of the shell 22 approximately directly opposite to the self-sealing valve 28. The purpose of the fill tube guide 54 is to serve as a seat for the stiffening rod or stylette (not shown) which is used to make the fill tube and balloon rigid during the original insertion of the balloon 20 into the stomach 26. In other words, before insertion the empty balloon 20 is mounted on the fill tube and stylette combination. The fill tube and stylette penetrate through the valve 28, and the stylette (not shown) is seated in the fill tube guide 54. The fill tube guide 54 prevents the shell 22 from being punctured by the stylette, when the collapsed balloon is being pushed down into the stomach.

As is shown on FIGS. 2 and 3, the fill tube guide 54 comprises a tubular body 58 having a flanged base 60. It can be affixed to the shell 22 with a patch 56 by vulcanization.

FIGS. 1, 2, 3, and 4 illustrate yet another novel feature of the intragastric balloon 20 of the present invention. A retrieval tab 64 is disposed on the exterior of the shell 22. The purpose of the tab 64 is to provide means through which the balloon 20 can be relatively easily captured or grasped after full or partial deflation and removed from the stomach 26. Preferably, the tab 64 is located on the pole 32. Alternatively, the tab 64 may be located on the equator 30.

Referring now particularly to FIGS. 2 and 4, in the preferred embodiment the tab 64 is affixed to a patch 66 which is used for filling the hole obtained in the process of manufacturing the shell 22. In other words, the patch 66 is vulcanized into the interior of the shell 22 to cover an opening in the shell 22. The patch 66 of the preferred embodiment is silicone rubber sheeting, approximately 40 mm in diameter and approximately 0.02 inch thick.

The retrieval tab 64 is cut into the appropriate shape shown on the drawings from substantially the center of a patch 68 of approximately 0.780 inch diameter, which is made from approximately 0.01 inch thick polyester fabric reinforced silicone rubber sheeting. The tab mounting patch 68 is affixed to the patch 66 by vulcanization or a suitable adhesive. The tab 64 has a small, narrow base 70 which is utilized for facilitating the capture of the tab 64 by a loop or snare (not shown) of a surgical instrument (not shown) utilized to remove the balloon 20 from the stomach 26. An X-ray opaque marker, which also serves as a visual marker, in the form of a black, tantalum metal containing dot 52, is also affixed to the inside of the retrieval tab 64. Locating the marker 52 here keeps the tab 64 from adhering to the surface of the shell 22 and facilitates capturing the tab 64 with a snare (not shown).

The several advantages of the above-described intragastric balloon should be readily apparent to those skilled in the art from the foregoing description. These advantages include the relative ease with which the balloon can be initially inserted into the stomach 26 by utilizing the fill tube guide 54, and the relative ease with which the important components of the balloon 20 can be visualized and manipulated while the balloon 20 is in the stomach 26. Finally, the retrieval tab 64 permits relatively easy withdrawal of the balloon 20 from the stomach 26.

Several modifications of the intragastric balloon of the present invention may become readily apparent to those skilled in the art in light of the foregoing disclosure. Therefore, the scope of the present invention should be interpreted solely from the following claims, as such claims are read in light of the disclosure.

What is claimed is:

1. An inflatable intragastric balloon useful for facilitating weight reduction when implanted into the stomach of obese patients, comprising:
    an inflatable shell, the shell having a smooth continuously convex exterior and a configuration such that when inflated the shell has a unique axis of greatest symmetry whereby when the inflated shell is placed into the interior of the stomach and disturbed while in the stomach, spinning of the shell about its axis of greatest symmetry causes minimum displacement of the walls of the stomach, and
    a self-sealing valve affixed to the shell at a predetermined location with respect to the axis of greatest symmetry, the balloon being inflatable through the valve by introduction of fluid into the balloon through the valve.

2. The intragastric balloon of claim 1 wherein the inflatable shell comprises a silicone elastomer.

3. The intragastric balloon of claim 2 wherein the silicone elastomer comprises high phenyl silicone.

4. The intragastric balloon of claim 1 wherein the valve is located on the periphery of the shell substantially on a plane which is orthogonal to the axis of greatest symmetry and substantially cuts the axis of greatest symmetry into two equal halves.

5. The intragastric balloon of claim 1 further comprising means located on the outer periphery of the shell for allowing capturing of the balloon to facilitate removal thereof from the stomach.

6. The intragastric balloon of claim 5 wherein the means for allowing includes an optical marker comprising a substantially non-reflective body.

7. The intragastric balloon of claim 5 wherein the means for allowing comprises a tab.

8. The intragastric balloon of claim 7 wherein the tab includes a black marker.

9. The intragastric balloon of claim 7 wherein the tab includes a narrow section for facilitating being captured for removal of the balloon from the stomach.

10. The intragastric balloon of claim 7 wherein the tab is reinforced.

11. The intragastric balloon of claim 1 wherein the means for allowing is located on the periphery of the shell substantially centered on the axis of greatest symmetry of the balloon.

12. The intragastric balloon of claim 1 wherein the interior surface of the shell is reinforced at least at one location adapted to receive a stylette introduced through the valve, said reinforcement comprising means for preventing accidental puncture of the shell by the stylette.

13. The intragastric balloon of claim 1 wherein the self-sealing valve comprises a tubular member having a flange at a first end, an interior passage and a substantially elastic membrane blocking the interior passage, and a collapsible tube mounted to the second end of the tubular member, the flange being affixed to the interior of the inflatable shell to align with an opening in the inflatable shell, the tubular member having larger internal diameter than the exterior diameter of a filler tube which is introduced through the valve for the purpose of introducing fluid into the balloon, the membrane having a substantially central opening which is significantly smaller in diameter than the filler tube and which nevertheless allows passage of the filler tube by expansion of the central opening.

14. The intragastric balloon of claim 13 wherein the self-sealing valve further includes a reinforcing member affixed to the exterior of the inflatable shell, the reinforcing member having a slot which is aligned with the opening in the inflatable shell.

15. The intragastric balloon of claim 14 wherein the slot of the reinforcing member is X-shaped.

16. An inflatable intragastric balloon useful for facilitating weight reduction when implanted into the stomach of obese patients, comprising:
    an inflatable elastomeric shell, the shell having a smooth continuously convex exterior and a configuration such that when inflated the shell has a single unique axis of greatest symmetry whereby when the inflated shell is placed into the interior of the stomach and disturbed while in the stomach, spinning of the shell about its axis of greatest symmetry involves minimum displacement of the walls of the stomach, and a self-sealing valve affixed to the shell at a location which is substantially on a plane orthogonal to the axis of greatest symmetry, which plane substantially cuts the axis of greatest symmetry into two equal halves, the balloon being inflatable through the valve by introduction of fluid into the balloon through the valve.

17. The intragastric balloon of claim 16 wherein the shell comprises a silicone elastomer.

18. The intragastric balloon of claim 16 further comprising means located on the exterior of the shell for allowing capturing of the balloon to facilitate removal thereof from the stomach.

19. The intragastric balloon of claim 18 having optically visible marker means located on the shell comprising substantially non-reflective material for facilitating identification of the positioning of the balloon with an endoscope when the balloon is in the stomach.

20. The intragastric balloon of claim 19 wherein the marker means are located adjacent to the valve.

21. The intragastric balloon of claim 16 having optically visible marker means located on the shell, comprising substantially non-reflective material for facilitating identification of the positioning of the balloon with an endoscope when the balloon is in the stomach.

22. The intragastric balloon of claim 21 wherein the marker means are located adjacent to the valve.

23. The intragastric balloon of claim 16 further comprising marker means located on the shell comprising substantially x-ray opaque material for facilitating identification of the positioning of the balloon when the balloon is in the stomach.

24. The intragastric balloon of claim 16 wherein the self-sealing valve comprises a reinforcing member affixed to the exterior of the inflatable shell and having a slot which registers with an opening in the inflatable shell, a tubular member having a flange at a first end, an interior passage and a substantially elastic membrane blocking the interior passage, and a collapsible tube mounted to the second end of the tubular member, the flange being affixed to the interior of the inflatable shell to register the interior passage with the opening in the inflatable shell, the tubular member having larger internal diameter than the exterior diameter of a filler tube which is introduced through the valve for the purpose of introducing fluid into the balloon, the membrane having a substantially central opening which is significantly smaller in diameter than the filler tube and which nevertheless allows passage of the filler tube by expansion of the central opening.

25. The intragastric balloon of claim 24 wherein the slot of the reinforcing member is X-shaped.

26. An inflatable intragastric balloon used for facilitating weight reduction when implanted into the stomach of obese patients, comprising:
an inflatable elastomer shell, the shell having a configuration such that when inflated the shell becomes substantially an ellipsoid having a smooth continuously convex exterior surface, whereby when the inflated shell is placed into the interior of the stomach and disturbed while in the stomach, spinning of the shell about its shortest axis involves minimum displacement of the walls of the stomach;
a self-sealing valve affixed to the shell substantially on the equator of the ellipsoid, the balloon being inflatable through the valve by introduction of fluid into the balloon through the valve, and
a tab affixed to the external periphery of the shell, the tab comprising means for allowing the capturing of the balloon for removal of the balloon from the stomach.

27. The intragastric balloon of claim 26 wherein the tab is located substantially on the pole of the ellipsoid.

28. The intragastric balloon of claim 27 having optically visible marker means located on the shell comprising substantially non-reflective material for facilitating identification of the positioning of the balloon with an endoscope when the balloon is in the stomach.

29. The intragastric balloon of claim 28 wherein the marker means are located adjacent to the valve.

30. The intragastric balloon of claim 29 wherein the marker means are also located on the tab.

31. The intragastric balloon of claim 30 wherein the shell comprises silicone elastomer.

32. The intragastric balloon of claim 31 wherein the shell comprises high phenyl silicone elastomer.

33. The intragastric balloon of claim 31 wherein the interior surface of the shell is reinforced at least at one location adapted to receive a stylette introduced through the valve, said reinforcement comprising means for preventing accidental puncture of the shell by the stylette.

34. The intragastric balloon of claim 31 wherein the tab and the area of the shell immediately adjacent to the tab is reinforced.

35. The intragastric balloon of claim 31 further comprising marker means located on the shell comprising substantially x-ray opaque material for facilitating identification of the positioning of the balloon when the balloon is in the stomach.

36. The intragastric balloon of claim 31, wherein the optically visible marker means are also opaque to x-ray.

37. The intragastric balloon of claim 26 wherein the self-sealing valve comprises an opening in the inflatable shell, a tubular member having a flange at a first end, an interior passage and a substantially elastic membrane blocking the interior passage, and a collapsible tube mounted to the second end of the tubular member, the flange being affixed to the interior of the inflatable shell to register the interior passage with the opening in the inflatable shell, the tubular member having larger internal diameter than the exterior diameter of a filler tube which is introduced through the valve for the purpose of introducing fluid into the balloon, the membrane having a substantially central opening which is significantly smaller in diameter than the filler tube and which nevertheless allows passage of the filler tube by expansion of the central opening.

38. The intragastric balloon of claim 37 wherein the self-sealing valve further comprises a reinforcing member affixed to the exterior of the inflatable shell and having a slot which registers with the opening in the inflatable shell.

39. The intragastric balloon of claim 38 wherein the slot of the reinforcing member is X-shaped.

40. The intragastric balloon of claim 26 wherein a visible marker is present substantially along the equator of the ellipsoid.

41. The intragastric balloon of claim 26 wherein the visible marker present substantially along the equator of the ellipsoid is also x-ray opaque.

* * * * *